(12) United States Patent
Frost

(10) Patent No.: US 9,499,465 B2
(45) Date of Patent: Nov. 22, 2016

(54) SYNTHESIS OF BIOBASED AND SUBSTITUTED TEREPHTHALIC ACIDS AND ISOPHTHALIC ACIDS

(71) Applicant: Board of Trustees of Michigan State University, East Lansing, MI (US)

(72) Inventor: John W. Frost, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 14/775,149

(22) PCT Filed: Mar. 14, 2014

(86) PCT No.: PCT/US2014/029422
§ 371 (c)(1),
(2) Date: Sep. 11, 2015

(87) PCT Pub. No.: WO2014/144843
PCT Pub. Date: Sep. 18, 2014

(65) Prior Publication Data
US 2016/0031787 A1    Feb. 4, 2016

Related U.S. Application Data

(60) Provisional application No. 61/798,968, filed on Mar. 15, 2013.

(51) Int. Cl.
| | | |
|---|---|---|
| C08G 63/00 | (2006.01) | |
| C07C 51/265 | (2006.01) | |
| C07C 51/353 | (2006.01) | |
| C07C 51/377 | (2006.01) | |
| C08G 63/183 | (2006.01) | |

(52) U.S. Cl.
CPC ........... C07C 51/265 (2013.01); C07C 51/353 (2013.01); C07C 51/377 (2013.01); C08G 63/183 (2013.01); C07C 2101/16 (2013.01); C07C 2102/44 (2013.01)

(58) Field of Classification Search
CPC .......................... C07C 51/353; C07C 51/377
USPC .......................................................... 528/308
See application file for complete search history.

(56) References Cited

U.S. PATENT DOCUMENTS

| 3,075,009 | A | 1/1963 | Keith et al. |
| 6,548,698 | B1 | 4/2003 | Grushin et al. |
| 2009/0203070 | A1 | 8/2009 | Devroe et al. |
| 2013/0071893 | A1 | 3/2013 | Lynch et al. |

FOREIGN PATENT DOCUMENTS

| EP | 2857509 A1 | 4/2015 |
| WO | WO-01/07387 A1 | 2/2001 |
| WO | WO-2010/101698 A2 | 9/2010 |
| WO | WO-2013/179722 A1 | 12/2013 |

OTHER PUBLICATIONS

International Search Report and Written Opinion of the ISA for PCT/US2014/029422, ISA/EP, mailed Aug. 7, 2014.
Kuehne, Martin E. et al: "Photochemical cyclization of olefinic N-chloroamides", The Journal of Organic Chemistry, vol. 40, No. 9, May 1, 1975 (May 1, 1975), pp. 1287-1292, XP055124609, ISSN: 0022-3263, DOI: 10.1021/jo00897a023 p. 1289, left column, paragraphs 6-7.
Akkari, Rhalid, et al: "(R)-or (S)-4-(3-hydroxy-4, 4-dimethyl-2-oxopyrrolidin-1-yl) benzoid acid as a new chiral auxiliary for solid phase asymmetric Diels-Alder reactions", Tetrahedron: Asymmetry, vol. 15, No. 16, Aug. 1, 2004 (Aug. 1, 2004), pp. 2515-2525, XP055124613, ISSN: 0957-4166, DOI: 10.1016/j.tetasy.2004.06.012, p. 2517, reaction of cpd. 11 to cpd. 12.
Parida, Keshaba Nanda, et al: "Oxidation of benzyl alcohols, benzyl halides, and alkylbenzenes with oxone", Tetrahedron, vol. 68, No. 47, Nov. 1, 2012 (Nov. 1, 2012), pp. 9763-9768, XP055124617, ISSN: 0040-4020, DOI: 10.1016/j.tet.2012.09.029, Table 3, entry 5.
Whited, Gregory M. et al: "Development of a gas-phase bioprocess for isoprene-monomer production using metabolic pathway engineering", Ind. Biotechnol., 2010; 6(3): pp. 152-163.
Kumar, Vinod et al: "Recent advances in biological production of 3-hydroxypropionic acid", Biotechnology Advances, 31 (2013) pp. 945-961.

*Primary Examiner* — Terressa Boykin
(74) *Attorney, Agent, or Firm* — Harness, Dickey & Pierce, P.L.C.

(57) ABSTRACT

Methods for producing bio-terephthalic acid and bio-isophthalic acid are provided. The methods comprise a cycloaddition reaction to produce bio-4-methyl-3-cyclohexene-1-carboxylic acid, and bio-3-methyl-3-cyclohexene-1-carboxylic from bio-isoprene and bio-acrylic acid. An aromatization reaction produces bio-para-toluic acid and bio-meta-toluic acid from the bio-4-methyl-3-cyclohexene-1-carboxylic acid, and bio-3-methyl-3-cyclohexene-1-carboxylic. An oxidation reaction produces the bio-terephthalic acid and iso-phthalic acid from the bio-para-toluic acid and bio-meta-toluic acid.

21 Claims, 4 Drawing Sheets

(65) TiCl4 (2 mol%), neat, rt, 94%, 23:1, para:meta. (70/70') 5% Pd on C, 240°C, 80 mm, 77%/69%. (75)/(75') Co(Oac)$_2$ (0.5 mol%), Mn(Oac)$_2$ (0.5 mol%), N-hydroxysuccinimide, O$_2$, HOAc, 100°C, 94%/88%.

SYNTHESIS OF BIOBASED AND SUBSTITUTED TEREPHTHALIC ACIDS AND ISOPHTHALIC ACIDS

CROSS-REFERENCE TO RELATED APPLICATIONS

This application is a 371 U.S. National Stage of International Application No. PCT/US2014/029422, filed Mar. 14, 2014, and published in English as WO 2014/144843 A1 on Sep. 18, 2014, which claims the benefit of U.S. Provisional Application No. 61/798,968, filed Mar. 15, 2013. The entire disclosures of the above applications are incorporated herein by reference.

STATEMENT OF GOVERNMENT INTEREST

This invention was made with government support under Grant No. CHE1213299 by the National Science Foundation. The government has certain rights in the invention.

INTRODUCTION

Plastic bottles are used to package a variety of consumer products, including food, beverage, cosmetic, personal care, and cleaning products. For example, on average, every person uses about 168 plastic water bottles every year, with over 100 million water bottles used worldwide every day. The U.S. population alone uses about 60 million plastic water bottles every day. In Europe, another 30 million plastic water bottles are used daily.

Increased concern regarding environmental problems and climate change has led to a heightened awareness of the composition of products, how they are made, and how they are disposed when they have reached the end of their useful lives. It takes about 700 years before plastic bottles begin to decompose, and it can take up to about 1000 years for a plastic bottle to fully decompose. Moreover, the plastic used in bottles is largely derived from petroleum, which is a non-renewable resource the supply of which can be subject to economic fluctuations and geopolitical concerns. Due to the environmental problems associated with manufacturing water bottles, large companies, such as Coca-Cola Co., Pepsi Co., Ford Motor Co., H. J. Heinz Co., Nike Inc. and Procter & Gamble Co. are trying to develop plant-based plastic packaging products.

Many food and beverage bottles are composed of petroleum-based poly(ethylene terephthalate) (PET). PET is manufactured by polymerization of terephthalic acid with ethylene glycol. Isophthalic acid is added to the polymerization at about 5% (by weight) to inhibit crystallization. The terephthalic acid and isophthalic acid used to synthesize PET are typically derived from xylene, which is isolated from BTX aromatics (benzene, toluene, and ortho-, meta-, and para-xylene) produced from crude oil. Over 150 billion liters of oil are used each year for plastic bottle manufacturing.

The cost and availability of materials used in PET may be affected by the overall economics of petroleum production relative to competing carbon sources. In particular, the increase in the production and use of shale gas around the world is adversely affecting the availability of certain petroleum based products. On a per million British thermal unit (BTU) basis, U.S. shale gas carbon is fourfold less expensive than crude oil carbon, and fivefold less expensive than carbon from maize. Consequently, production resources in the refining and petrochemical industry are shifting from petroleum to shale gas, decreasing the production of BTX aromatics. For example, the closure of Sunoco's Marcus Hook refinery in Pennsylvania alone removed about 19,000 barrels per day of aromatics from the market. The result from these market forces is to increase the cost of PET as the supply of BTX aromatics decreases.

As an alternative to synthesizing PET from petrochemicals, terephthalic acid and isophthalic acid can be synthesized from isoprene and acrylic acid. A synthesis of terephthalic acid and isophthalic acid involves a pathway that begins with a cycloaddition reaction between isoprene and acrylic acid that yields 3-methyl-3-cyclohexene-1-carboxylic acid and 4-methyl-3-cyclohexene-1-carboxylic acid. These products can be ultimately converted to terephthalic acid and isophthalic acid. It has been found that this synthetic pathway may be an economically advantageous route to produce these materials for use in manufacturing PET and other industrial chemicals, since the starting materials can be produced from renewable resources. Until recently there were no bio-based sources of isoprene and acrylic acid. However, a joint venture between Ajinomoto, Inc. and Bridgestone Corp. has led to a development of bio-isoprene, which is used to manufacture synthetic rubber for tires. Bio-isoprene is produced by fermenting microbes growing in a biomass feedstock. Additionally, OPX Biotechnologies, Inc. has developed bio-acrylic acid, also by fermenting genetically modified microbes on a biomass feedstock of dextrose (corn) or sucrose (cane).

Nevertheless, the art does not provide a method to use bio-isoprene and bio-acrylic acid can be used to generate bio-terephthalate and bio-isophthalate in an efficient and cost-effective manner. There remains a need to manipulate the pathway in order to effectively generate terephthalic acid and isophthalic acid, particularly in the desired relative yields so as to be used in producing PET. Such a method would enable the production of PET packaging having 100% carbon content derived from renewable feedstocks.

SUMMARY

The present technology provides methods for producing terephthalic acid and isophthalic acid. The method comprises a cycloaddition reaction of isoprene and acrylic acid to produce 3-methyl-3-cyclohexene-1-carboxylic acid and 4-methyl-3-cyclohexene-1-carboxylic acid, aromatization to produce meta- and para-toluic acid, and oxidation to produce isophthalic and terephthalic acid. In various embodiments, the isoprene and acrylic acid are bio-based.

In various embodiments, the cycloaddition reaction is catalyzed. Suitable catalysts include Lewis acids. A preferred catalyst comprises Ti, such as $TiCl_4$. Preferably the cycloaddition is a neat reaction.

In various embodiments, the aromatization reaction is conducted using sulfuric acid or catalysts conventionally used in vapor phase dehydrogenation or oxidation reactions. In a preferred embodiment, the aromatization is a vapor phase dehydrogenation using a Pd catalyst, such as Pd(0) on carbon. Catalysts for the oxidation reaction include N-hydroxyphthalimide (NHPI), N-hydroxysuccinimide (NHSI), N-hydroxymaleimide (NHMI), N-hydroxy-1,8-naphthalimide (NHNI), and carbonic acid tert-butyl phthalimido ester (CATPE).

Figure 1:
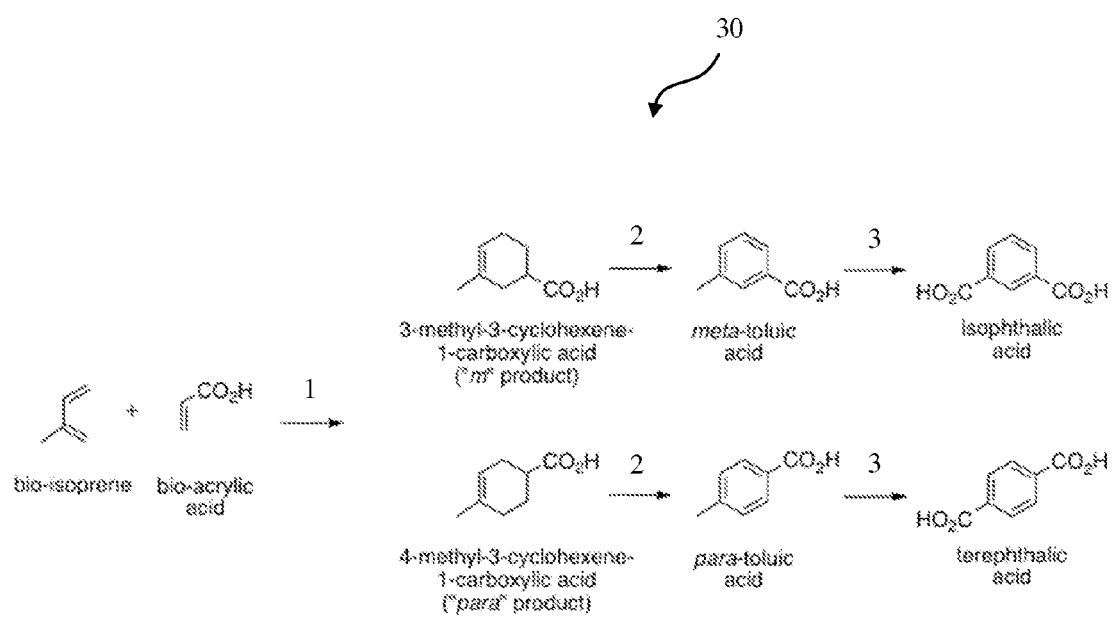
FIG. 1 is a reaction scheme for bio-terephthalic acid production and bio-isophthalic acid production comprising a cycloaddition reaction of the present invention.

Corresponding reference numerals indicate corresponding parts throughout the several views of the drawings. It should be noted that the figures set forth herein are intended to exemplify the general characteristics of materials, compositions, devices, and methods among those of the present technology, for the purpose of the description of certain embodiments. These figures may not precisely reflect the characteristics of any given embodiment, and are not necessarily intended to fully define or limit specific embodiments within the scope of this technology.

DESCRIPTION

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

FIG. 1 shows a reaction scheme for the production of terephthalic acid and isophthalic acid. The scheme comprises a cycloaddition, an aromatization, and an oxidation. The meta product of the cycloaddition reaction 3-methyl-3-cyclohexene-1-carboxylic acid and the para product is 4-methyl-3-cyclohexene-1-carboxylic acid. When bio-isoprene and bio-acrylic acid are the starting reactants, terephthalic acid and isophthalic acid are downstream products of the para and meta products of the cycloaddition, respectively.

In various embodiments, the isoprene and acrylic acid are bio-based, i.e., are bio-isoprene and bio-acrylic acid, to make bio-based terephthalic acid and isophthalic acid. As referred to herein, "bio-based" materials are made from substantially renewable resources, produced or synthesized using at least one starting material that is not derived from a fossil fuel (e.g., petroleum, coal, and natural gas). Bio-based materials may be made from plant materials or through fermentation or other microbial production processes.

Bio-isoprene may be made, for example, from fermenting microbes growing in a biomass feedstock. For example, Whited et al. (Ind. Biotechnol., 2010; 6(3):152-163) describe various platforms for generating bio-isoprene from in engineered bacteria from renewable feedstocks. These platforms include engineered recombinant bacteria that have a heterologous isoprene synthase gene, which is derived from plants. Also, Hayashi et al. (International Publication No. WO 2013/179722, published Dec. 5, 2013) describe methods for producing bio-isoprene monomer in various bacteria and fungi with various saccharides as a source of carbon. These methods include engineering bacteria and fungi with an isoprene synthase gene from plants, which enables the bacteria and fungi to biosynthesize isoprene. Whited et al. and Hayashi et al. are both incorporated herein by reference in their entirety.

Bio-acrylic acid, may be made by fermenting genetically modified microbes on a biomass feedstock of dextrose (corn) or sucrose (cane). For example, Kumar et al. (Biotechnol. Adv., 2013; 31:945-961) describe various methods for synthesizing 3-hydroxypropionic acid (3-HP), which can be converted into acrylic acid, from various prokaryotes and eukaryotes. Also, Devroe et al. (U.S. Patent Application Publication No. 2009/0203070, published Aug. 13, 2009) describe methods for producing bio-acrylic acid from hyper-photosynthetic organisms, such as various plants, algae, and bacteria. Additionally, Lynch et al., (U.S. Patent Application Publication No. 2013/0071893, published Mar. 21, 2013), describe a process for generating bio-acrylic acid from recombinant bacterial and yeast microorganisms, which rely on various monosaccharides (such as glucose and fructose), oligosaccharides (such as lactose and sucrose), and polysaccharides (such as starch and cellulose) as sources of carbon. Kumar et al., Devroe et al, and Lynch et al. are all incorporated herein by reference in their entirety.

In various embodiments, the terephthalic acid and isophthalic acid made by the methods of the present invention polymerized with ethylene glycol to yield poly(ethylene terephthalate) (PET). PET may be used, for example, in making fibers, packaging, such as food and beverage containers and bottles. In some embodiments, methods comprise reacting bio-isoprene with a substituted bio-alkene, so as to make substituted terephthalates and isophthalates. Such materials may be used, for example, as performance-enhancing additives in polyester applications.

(1) Cycloaddition

Methods of the present technology comprise a Diels-Alder cycloaddition reaction in which a diene reacts with a dienophile (a substituted or unsubstituted alkene) to form a substituted or unsubstituted cyclohexene product. In some embodiments, the cycloaddition reaction includes a bio-diene and/or a bio-dienophile. The diene can be isoprene or bio-isoprene. The dienophile can be an alkene, a bio-alkene, a substituted alkene, a substituted bio-alkene, acrylic acid, or bio-acrylic acid. In one embodiment, the diene is bio-isoprene and the dienophile is bio-acrylic acid. Referring again to FIG. 1, when the diene is bio-isoprene and the dienophile is bio-acrylic acid, bio-isoprene and bio-acrylic acid undergo a cycloaddition reaction to form 4-methyl-3-cyclohexene-1-carboxylic acid (the para product) and 3-methyl-3-cyclohexene-1-carboxylic acid (the meta product). In some embodiments, the cycloaddition reaction is performed to yield a para-product:meta-product ratio that ultimately yields a terephthalic acid:isophthalic acid ratio useful for PET production. For example, because the synthesis of PET requires about 95% terephthalic acid and about 5% isophthalic acid, in various embodiments the cycloaddition reaction is performed to result in a para product:meta product ratio of about 10:1. In other embodiments, the para:meta product ratio is about 100:1, about 90:1, about 80:1, about 70:1, about 60:1, about 50:1, about 40:1, about 30:1, about 25:1, about 20:1, about 15:1, about 10:1, about 9.5:1, about 9:1, about 8.5:1, about 8.0:1, about 7.5:1, or about 7.0:1. In a preferred embodiment, the cycloaddition reaction produces 100% para product.

Optionally, the ratio of para to meta products produced from the cycloaddition reaction is controlled by use of a catalyst. For example, with no catalyst present, combining isoprene and acrylic acid (collectively, the "reaction mixture") at a 1:1 molar ratio and then autoclaving at 95° C. for about 2 hours results in the production of 75:25 para:meta product. By repeatedly recrystallizing the para product from cold hexane (0° C.-5° C.), pure para product can be isolated at about a 59% yield. In some embodiments, the cycloaddition reaction is performed under pressure. The pressure can be from about 75 psi to about 200 psi. In some embodiments, the pressure is changed over time. In yet other embodiments, heat is added to the reaction from about 80° C. to about 95° C. For example, the cycloaddition reactants can be pressurized to about 120 psi under $N_2(g)$. The reaction mixture can then be heated to about 95° C. and stirred for about 2 hours at about 150 psi. When the 2 hours expires, the reaction mixture can be cooled. As mentioned, the products can be recrystallized from hexane and purified.

Various catalysts can be used to influence the ratio of para:meta products formed form the cycloaddition reaction. Preferably, the cycloaddition reaction is conducted using a Lewis acid catalyst. In some embodiments, the Lewis acid catalyst is an ionic liquids, such as pyridinium-based 1-ethyl-pyridinium tetrafluoroborate ($[EtPy]^+[BF_4]^-$) and 1-ethyl-pyridinium trifluoroacetate ($[EtPy]^+[CF_3COO]^-$). Using $[EtPy]^+[BF_4]^-$ or $[EtPy]^+[CF_3COO]^-$ as solvents for isoprene and acrylic acid and incubating for about 2 hours can result in para:meta product ratios of 82:18 and 95:5 respectively.

Boronic acid catalysts can be also used to manipulate cycloaddition products. In the cycloaddition reaction 1, isoprene and acrylic acid can be combined in about a 2:1 ratio in water and dichlormethane (DCM). Performing the reaction with 2-bromophenyl boronic acid as a catalyst for about 48 hours at room temperature can yield about 91:4 para:meta products.

Catalysis leading to acyloxyborane and acylboronate intermediacy can enhance para selectivity in the cycloaddition of acrylic acid and isoprene. Use of $BH_3$ (15 mol %) and 2-bromophenylboronic acid (20 mol %) affords 80-90% yields of 4-methyl-3-cyclohexene-1-carboxylic acid (para product) cycloaddition product in $CH_2Cl_2$. However, the solvent choice, relatively high mol % catalyst requirement, and the multiple steps/expense for synthesis of $BH_3$ and 2-bromophenylboronic acid detracts from their potential utility in commodity chemical synthesis. Lewis acid catalysis of the cycloaddition is an attractive alternative.

In various embodiments, the cycloaddition reaction is catalyzed using a Lewis acid catalyst comprising aluminum, copper, hafnium, magnesium, nickel, iron, yttrium, zinc, zirconium, scandium, tin, or titanium anions. Because of their ability to modulate Lewis acidity, triflates, chlorides, and bromides can be used as counteranions. For example, Lewis acids useful herein may be selected from the group consisting of $CuCl$, $CuCl_2$, $NiCl_2$, $YCl_3$, $FeCl_2$, $AlCl_3$, $FeCl_3$, $ZnCl_2$, $MgCl_2$, $TiCl_3$, $SnCl_4$, $ScCl_3$, $SnCl_2$, $HfCl_4$, $ZrCl_4$, and $TiCl_4$. In some embodiments, $Cu^{2+}$, $Fe^{3+}$, and $Sn^{2+}$ can result in violent reactions, which require an addition of diisopropylethylamine (DIPEA), triethyl amine, or lutidine, to avoid. In some embodiments, however, violent reactions are avoided by the use of chloride as the counter anion, without the addition of DIPEA, triethyl amine, or lutidine. A preferred Lewis acid catalyst is $TiCl_4$.

In various embodiments, the cycloaddition is conducted under neat conditions, i.e., as a reaction conducted essentially without solvents. Such reaction conditions are advantageous, avoiding potential toxicity, volatility, and recycling issues that may be associated with solvent use. Therefore, in various embodiments, the cycloaddition reaction can be performed under neat reaction conditions in the presence of a catalyst, such as a Lewis acid catalyst. In a preferred embodiment, the cycloaddition of isoprene and acrylic acid is a neat reaction using $TiCl_4$ as a catalyst.

Neat reactions can be performed, for example, by first adding acrylic acid to the Lewis acid, followed by addition of isoprene. The acrylic acid is added to the Lewis acid under an inert gas, such as Ar, Ne, or He, although the use of inert gas is not required for the subsequent addition of isoprene. The reaction may be conducted at a temperature from about −30° C. to about 30° C. In various embodiments, the reaction proceeds for from at least about 1 hour, at least about 10 hours, or at least about 24 hours. In various embodiments, the reaction proceeds for about 120 hours or less, for about 100 hours or less, or for from about 48 hours or less. In one embodiment, the reaction proceeds for about 24 hours. In some embodiments, the reaction is conducted at from about −25° C. to about 5° C. for from about 24 hours to about 120 hours, or from about −20° C. to about 0° C. for from about 48 hours to about 100 hours. In some embodiments, the reaction is conducted at ambient (room temperature) conditions (i.e., at from about 20° C. to about 25° C.), for from about 1 hour to about 48 hours. In some embodiments, the reaction is initiated at a reduced temperature, such as from about −20° C. to about 0° C., and then allowed to warm to room temperature where the reaction proceeds for from about 1 hour to about 48 hours.

(2) Aromatization

With reference to FIG. 1, the aromatization reaction can be a solvent phase reaction, an oxidative dehydrogenation, or a vapor phase reaction. For example, the aromatization may comprise an $H_2SO_4$ oxidation of the para and meta cycloaddition products to form para-toluic acid and meta-toluic acid. In an $H_2SO_4$ oxidation, concentrated sulfuric acid may be added dropwise to one or both of 4-methyl-3-cyclohexene-1-carboxylic acid and 3-methyl-3-cyclohexene-1-carboxylic acid to form a mixture. The mixture can be heated from about 80° C. to about 100° C. for about 5 minutes to about 20 minutes with vigorous bubbling of $SO_2$. Cessation of $SO_2$ bubbling marks the completion of the reaction. The reaction mixture is then poured into ice to precipitate solid toluic acid, which can be collected by vacuum filtration to isolate a filtrate. The filtrate can be extracted with ethyl acetate (EtOAc), from 1 to about 5 times, and organic layers are combined, dried over $MgSO_4$, and concentrated to form a toluic acid concentrate. The concentrate can be dissolved in EtOAc and filtered through a plug of silica gel to isolate a EtOAc filtrate, followed by washing of the silica gel with EtOAc. In another embodiment, the concentrate is distilled through silica gel, such as in a Kugelrohr distillation procedure. The EtOAc filtrate can be concentrated and recrystallized to afford purified toluic acid.

As mentioned above, the aromatization reaction can involve a vapor phase catalytic dehydrogenation of the para and meta cycloaddition products to form para-toluic acid and meta-toluic acid. Catalysts used in the aromatization reaction include such catalysts that are known in the art for use in catalytic dehydrogenation or catalytic oxidation reactions. Catalysts include chromium, molybdenum, iridium, rhodium, ruthenium, nickel, palladium, platinum, vanadium, iron, and manganese. In some embodiments, the catalyst is nickel, platinum or palladium.

In various embodiments, the aromatization reaction is catalyzed by a catalyst on a substrate. The substrate can be carbon, silica, alumina, titania, or zirconia. In a preferred embodiment, the catalyst is a Pd(0) on carbon (Pd/C) catalyst. For example, a Pd/C catalyst can be added to one or both of 4-methyl-3-cyclohexene-1-carboxylic acid and 3-methyl-3-cyclohexene-1-carboxylic acid to form a suspension. For example, the suspension can be refluxed for about 3 hours to about 8 hours under air, and then filtered through Celite®, commercialized by Sigma-Aldrich Co. (St. Louis, Mo.), to produce a filtrate. Concentrating the filtrate results in formation toluic acid residue. The dehydrogenation may be conducted at temperatures ranging from about 35° C. to about 500° C., or from about 100° C. to about 400° C. at from about 1 mm to about 750 mm of pressure. In one embodiment, a para cycloaddition product is distilled at from about 50 mm to about 100 mm and from about 100° C. to about 300° C. through Pd on C dispersed in macroporous silica gel. In another embodiment, a homogenous oxidation of para cycloaddition product is performed in mesitylene at from about 75° C. to about 150° C. under $O_2$ catalyzed by Pd(triflate)$_2$, unliganded or liganded with 2-dimethylaminopyridine. In yet another embodiment, a vapor phase dehydrogenation of a 2.5:1 mixture of para:meta product resulting from an uncatalyzed cycloaddition is performed using Pd(0) on C.

In other embodiments, Pd (II) trifluoroacetic acid (Pd (TFA)$_2$), p-toluenesulfonic acid, mesitylene, and 2-(dimethylamino)pyridine are added to one or both of 4-methyl-3-cyclohexene-1-carboxylic acid and 3-methyl-3-cyclohexene-1-carboxylic acid to form a mixture. The mixture can be sparged with $O_2$(g) for about 10 minutes to about 20 minutes, and then heated to from about 80° C. to about 100° C. for about 36 hours to about 54 hours. The mixture can then be filtered to form a filtrate, and the filtrate can be concentrated to toluic acid residue.

(3) Oxidation

With reference to FIG. 1, the oxidation reaction is performed to oxidize p- and m-toluic acid to form terephthalic acid and isophthalic acid. In various embodiments, a Amoco Mid-Century oxidation is conducted. Commercially, such oxidation methods are used to convert p-xylene into terephthalic acid. In the present methods, a Co(OAc)$_2$/Mn(OAc)$_2$ catalyst in acetic acid solvent using air as the oxidant and an alkyl halide as a radical chain carrier may be used under high pressure reaction conditions.

In the oxidation reaction, N-hydroxyimides can be used in the presence of metallic salts, to avoid elevated temperatures. Preferred N-hydroxyimides include N-hydroxyphthalimide (NHPI), N-hydroxysuccinimide (NHSI), N-hydroxymaleimide (NHMI), N-hydroxy-1,8-naphthalimide (NHNI), and carbonic acid tert-butyl phthalimido ester (CATPE). Non-limiting examples of metallic salts include Co(II) acetate tetrahydrate, and Mn(OAc)$_2$.

For example, N-hydroxysuccinimide can be used to enable the oxidation of p-toluic acid 5 catalyzed by Co(OAc)$_2$/Mn(OAc)$_2$ in acetic acid solvent to proceed under 1 atm $O_2$ at 100° C. and affords terephthalic acid (94%) and 4-formylbenzoic acid (1%) with 1% unreacted p-toluic acid. Oxidation of m-toluic acid leads to isophthalic acid 8 in 88% yield. p-Toluic acid and m-toluic acid are significantly more reactive than p-xylene under identical reaction conditions. p-Xylene oxidation leads to terephthalic acid (69%), 4-formylbenozoic acid (3%), and p-toluic acid 5 (5%).

In various embodiments, toluic acid, an N-hydroxyimide, at least one metallic salt and glacial acetic acid are mixed together in a reactor to form a mixture. The mixture is purged under $N_2$(g) or $O_2$(g) with stirring and heat is applied to from about 80° C. to about 100° C. Pure $O_2$ is added to the reactor and the mixture is incubated for from about 12 to about 36 hours. Upon completion of the reaction, solid terephthalic acid and/or isophthalic acid products and mother liquor are separated by filtration.

Substituted Aromatics

As described above, the route from bio-isoprene to bio-terephthalic acid exploits a cycloaddition reaction, which is one of the most versatile routes leading to substituted aromatics. Therefore, reaction of the diene isoprene with dienophiles other than acrylic acid provides a route to substituted terephthalates. For example, in various embodiments, biobased isoprene is reacted with biobased cinnamic acid to lead to biobased phenylterephthalic acid, which is a substituted terephthalate additive that imparts unique properties to liquid crystalline polymers. In another embodiment, biobased isoprene is reacted with biobased fumaric or maleic acids to lead to trimellitic acid, which in its esterified form, is used as a high performance plasticizer in wire and cable insulation. Similarly, reaction of isoprene with dienophiles other than acrylic acid leads to substituted isophthalates.

Production of PET

Figure 4:
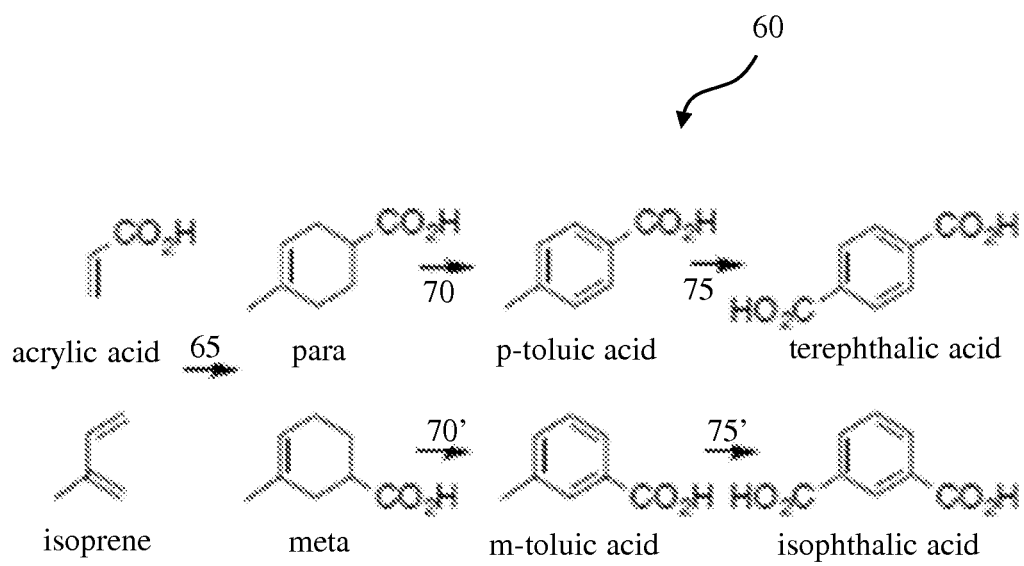
FIG. 4 is an exemplary reaction scheme, comprising a cycloaddition reaction of the present invention, showing catalysts and reactions conditions.

FIG. 4 shows an exemplary reaction scheme, which generates terephthalic acid and isophthalic acid with high yields. As shown in the figure, the scheme includes a neat cycloaddition reaction, which comprises a reaction with acrylic acid and isoprene with a TiCl4 catalyst at room temperature, which results in a 94% yield of 23:1 para:meta products. In aromatization reactions, the para and meta products are reacted with Pd on C at 240° C. and 80 mm to afford a 77% yield of p-toluic acid and a 69% yield of m-toluic acid. Then in oxidation reactions, the p- and m-toluic acid react with a Co(OAc)$_2$ (0.5 mol %)/Mn(OAc)$_2$ (0.5 mol %) catalyst in acetic acid with a N-hydroxysuccinimide radical chain carrier, under $O_2$ gas, at 100° C., to afford a terephthalic acid yield of 94% and a isophthalic acid yield of 88%. The resulting materials may be used directly in production of PET, having a desired ratio of terephthalic acid and isophthalic acid.

By starting with one or both of bio-isoprene and bio-acrylic acid, PET can be synthesized in whole or in part from renewable feedstocks. In some embodiments, PET may be made using bio-terephthalic acid with petroleum-based isophthalic acid. Alternatively, PET may be made using petroleum based terephthalic acid with bio-isophthalic acid.

Where the acrylic acid is bio-acrylic acid and the isoprene is bio-isoprene, the scheme results in the synthesis of bio-terephthalic acid, bio-isophthalic acid, or mixtures thereof. Bio-isophthalic acid and bio-terephthalic acid can react with ethylene glycol to generate bio-PET, which can be used in the manufacture of plastic for use in, for example, plastic packaging or fibers. Where the ethylene glycol is bio-ethylene glycol, PET can be generated with 100% of its carbon content derived from renewable feedstocks.

The present technology provides PET made by a process comprising:
  (a) reacting isoprene with acrylic acid in the presence of a first catalyst to produce 4-methyl-3-cyclohexene-1-carboxylic acid and 3-methyl-3-cyclohexene-1-carboxylic acid;
  (b) performing an aromatization reactions on the 4-methyl-3-cyclohexene-1-carboxylic acid and the 3-methyl-3-cyclohexene-1-carboxylic acid to produce bio-para-toluic acid and bio-meta-toluic acid;
  (c) performing an oxidation reaction on the para-toluic acid and the meta-toluic acid in the presence of a third catalyst to form terephthalic acid and isophthalic acid; and
  (d) polymerizing the terephthalic acid and the isophthalic acid with ethylene glycol to produce PET.

In various embodiments, one or both of the isoprene and acrylic acid are bio-based, so as to produce bio-terephthalic acid and isophthalic acid, and thereby produce bio-PET. Preferably, the terephthalic acid and isophthalic acid are produced at a terephthalic acid:isophthalic acid ratio of from about 90:10 to about 99:1, such as a ratio of about 97:3 or about 95:5. In some embodiments, the PET made by the process comprises cis/trans cyclohexane carboxylic acid.

Figure 2:
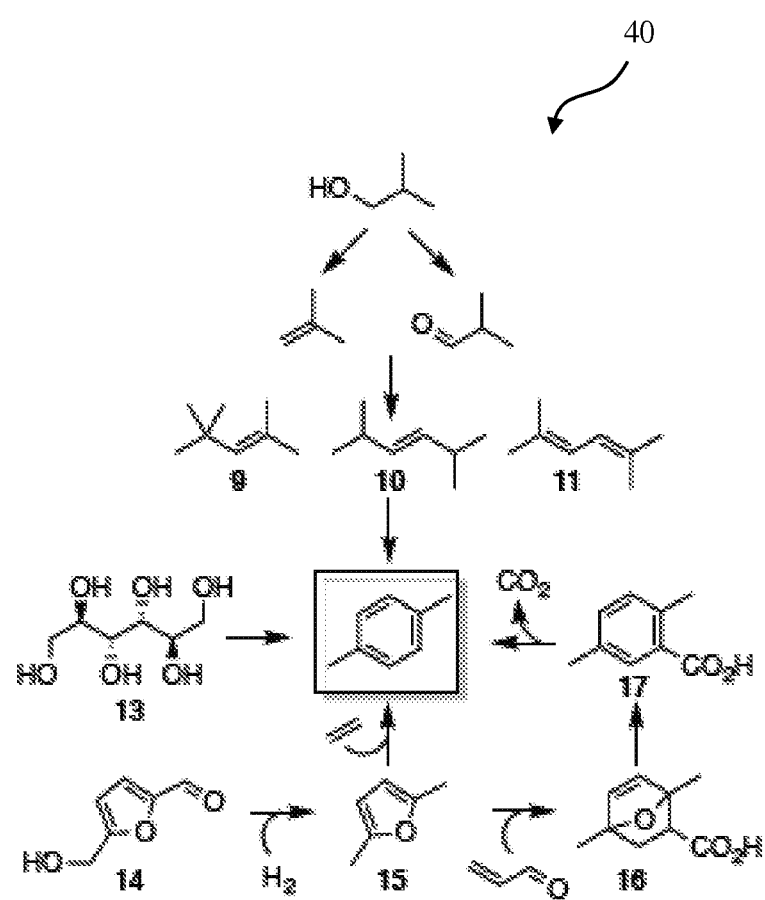
FIG. 2 is a second reaction scheme, which shows a syntheses of biobased terephthalic acid with p-xylene intermediacy.
Figure 3:
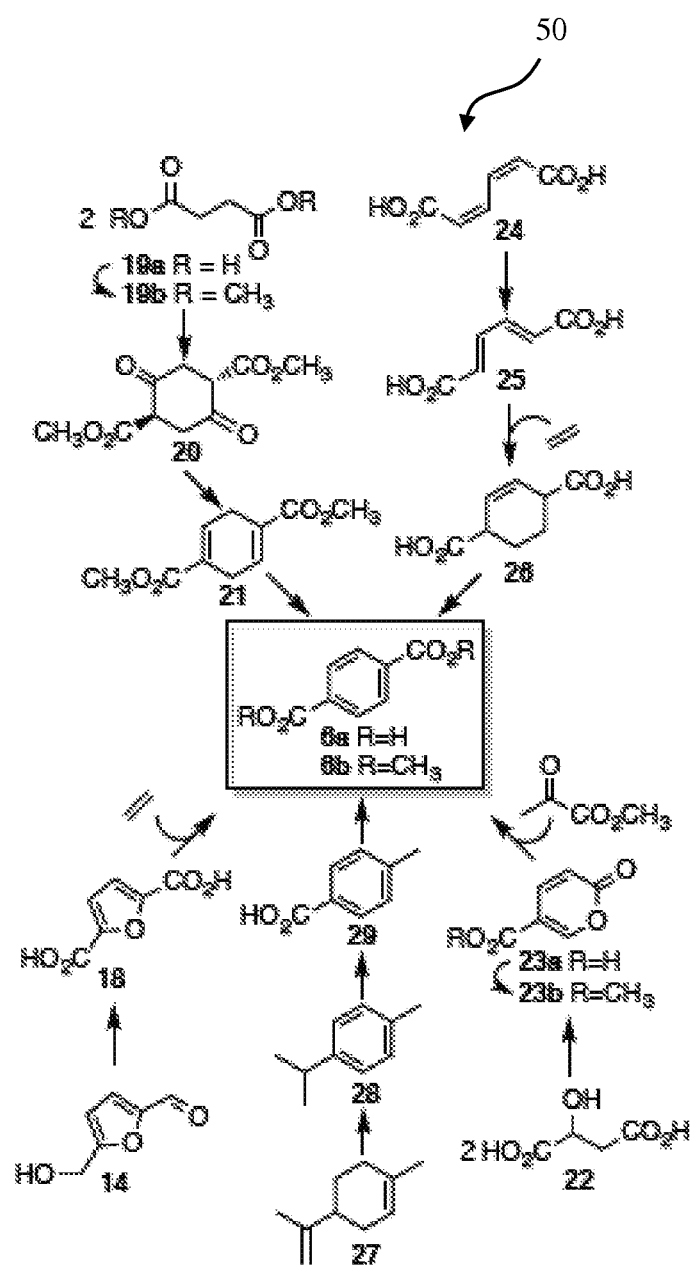
FIG. 3 is a third reaction scheme, which shows a syntheses of biobased terephthalic acid without p-xylene intermediacy.

Alternative routes to producing biobased terephthalic acid are depicted in FIGS. 2 and 3. For example, FIG. 2, depicts a synthesis that does not employ a p-xylene intermediate. As shown in FIG. 2, isobutanol (microbially synthesized from glucose) is dehydrated to isobutene or oxidized to isobutanal. Dimerization of isobutene leads to 2,4,4-trimethylpentenes, which undergo catalyzed dehydrocyclization to pxylene at 550° C. Alternatively, isobutene can be dimerized, reacted with isobutanol, or reacted with isobutanal. The resulting 2,5-dimethyhexenes or 2,5-dimethylhexadienes undergo dehydrocyclization to p-xylene at 450° C. p-Xylene can also be obtained from 2,5-dimethylfuran. Cycloaddition with ethene and dehydration of the resulting bicycle adduct affords p-xylene. Cycloaddition of 2,5-dimethylfuran with acrolein followed by an oxidation, dehydration, and decarboxylation leads to p-xylene. 2,5-Dimethylfuran is obtained by hydrogenation of 5-hydroxymethylfurfural, which is chemically derived from glucose or fructose. Catalytic reforming of polyols such as glucose-derived sorbitol over Pt—Re followed by Ru on C hydrogenation and final transformation over H-ZSM-5 affords a mixture of aromatics including p-xylene.

FIG. 3 depicts a synthesis that uses a p-xylene intermediate. As shown in FIG. 3, oxidation of 5-hydroxymethylfurfural 14 to 2,5-furandicarboxylic acid 18 followed by cycloaddition with ethene enables a short, albeit low-yielding route to biobased terephthalic acid 6a. Dimerization of dimethyl succinate 19b, which is derived from esterification of succinic acid 19a (microbially synthesized from glucose), affords dimethyl disuccinate 20. Hydrogenation and dehydration gives dihydroterephthalate 21 that disproportionates to a mixture of products including dimethyl terephthalate 6b. Dimerization of malic acid 22 (microbially synthesized from glucose) followed by esterification affords methyl coumalate 23b. Cycloaddition of 24b with methyl pyruvate leads to dimethyl terephthalate 6b. Routes starting with succinic and malic acids require a final hydrolysis to obtain 6a. Isomerization of cis,cis-muconic acid 24 (microbially synthesized from glucose), cycloaddition of the resulting trans,trans-muconic acid 25 with ethene, and dehydrogenation of 26 leads to 6a. Conversion of biobased limonene 27 to p-cymene 28 is followed by stepwise oxidation of the side chains to give 6a. 2,5-Furandicarboxylic acid is 18 also a monomer for synthesis of poly(ethylene 2,5-furandicarboxylate) (PEF), which is a polyester substitute for PET. Unlike PET, recycling of PEF is problematic.

In comparison to the routes summarized in FIGS. 2 and 3, the cycloaddition reaction sequence (FIGS. 1 and 4) affords the highest overall yield of terephthalic acid from biobased starting material. Esterification and subsequent hydrolysis to obtain biobased terephthalic acid is avoided. Temperatures in excess of 250° C. and the use of high-pressure reaction vessels are avoided. Purifications of cycloaddition and aromatization intermediates are simple and avoid multistep procedures. Two of the three steps require no solvents. Final oxidation of p-toluic acid employs the same solvent and catalysts used in commercial oxidation of p-xylene. The cycloaddition reaction sequence (FIGS. 1 and 4) and biobased isobutanol are the only routes that enable synthesis of biobased isophthalic acid.

The compositions and processes of the present technology are illustrated in the following non-limiting examples.

NMR Spectroscopy and Reagents $^1$H NMR spectra were recorded on a 500 MHz spectrometer. Chemical shifts for $^1$H NMR spectra were reported (in parts per million) relative to CDCl$_3$ ($\delta$=7.26 ppm). $^{13}$C NMR spectra were recorded at 125 MHz and the shifts for these spectra were reported (in parts per million) relative to CDCl$_3$ ($\delta$=77.0 ppm). GC spectra were recorded on an Agilent 6890N chromatograph equipped with an autosampler. MnBr$_2$, SnBr$_2$, and Sn(OTf)$_2$ were purchased from Alfa Aesar (Ward Hill, Mass.) while CuBr, Cu(OTf)$_2$, Fe(OTf)$_2$, MgBr, ScCl$_3$, and Zn(OTf)$_2$ were purchased from Strem (Newburyport, Mass.). All other reagents were purchased from Sigma-Aldrich (St. Louis, Mo.). Chemicals were used as received without further purification.

EXAMPLE 1

4-Methylcyclohex-3-ene-1-carboxylic Acid and 3-Methylcyclohex-3-ene-1-carboxylic Acid Isoprene (36.4 g, 535 mmol) was added to acrylic acid (35.3 g, 489 mmol) to form a reaction mixture and pressurized to 120 psi under N$_2$ in a Parr Series 4575 high pressure reactor interfaced with a Series 4842 temperature controller. The reaction mixture was heated to 95° C. and stirred (100 rpm) for 2 hours at 150 psi after which the reaction mixture was allowed to cool.

The reaction afforded a yellow, heterogeneous mixture containing a 2.5/1 (mol/mol) mixture of 4-methylcyclohex-3-ene-1-carboxylic acid and 3-methylcyclohex-3-ene-1-carboxylic acid $^1$H NMR (CDCl$_3$): $\delta$ 5.359 (s, 1H), 2.510 (m, 1H), 2.210 (m, 2H), 2.000 (m, 3H), 1.709 (m, 1H), 1.633 (s, 3H) for 4-methylcyclohex-3-ene-1-carboxylic acid; $\delta$ 5.377 (s, 1H), 2.592 (m, 1H), 2.210 (m, 2H), 2.000 (m, 3H), 1.654 (s, 3H), 1.598 (m, 1H) for 3-methylcyclohex-3-ene-1-carboxylic acid. Crude product was submitted to repeat crystallizations from hexanes to obtain pure 4-methylcyclohex-3-ene-1-carboxylic acid. The first crystallization from hexane afforded 17.2 g of white, crystalline. Filtrate was concentrated and crystallized at 0° C. from hexane to afford 6.5 g of a 2nd crop of white, crystalline. Filtrate from the 2nd crop was concentrated and crystallized at −20° C. to afford 11.5 g of a 3rd crop of white, crystalline. Filtrate from the 3rd crop was concentrated and crystallized at −20° C. to afford 3.2 g of a 4th crop of white, crystalline. Filtrate from the 4th crop was concentrated and crystallized at −20° C. to afford 0.8 g of a 5th crop of white, crystalline. A total of 39 g (56% yield) of pure 4-methylcyclohex-3-ene-1-carboxylic acid was obtained from the five crystallizations.

EXAMPLE 2

Cycloaddition Reactions

Derivatization of Cycloaddition Products for GC Analysis.

A weighed quantity of cycloaddition reaction products (50.0 mg, 0.357 mmol) was added to a 10 mL volumetric flask. Decane internal standard (0.02 mL, 0.1 mmol) and N,O-bis(trimethylsilyl)trifluoroacetamide (BSTFA) (1.5 mL, 5.59 mmol) were then added. Derivatization was complete upon mixing. The solution was then diluted with toluene to 10 mL. Syringe filtration (0.45 µm Whatman filter) was followed by analysis to determine the ratio of para and meta cycloaddition products.

Derivatized samples were analyzed using an Agilent HP-5 (5%-Phenyl)-methylpolysiloxane coated capillary column (30 m×0.320 mm i.d.×0.25 µL film thickness) to determine the ratio of 4-methylcyclohex-3-enecarboxylic acid (para product) and 3-methylcyclohex-3-enecarboxylic acid (meta product). A second sample was prepared for GC without BSTFA derivatization and analyzed using an Agilent DB-FFAP nitroterephthalic acid modified polyethylene glycol coated capillary column (30 m×0.320 mm i.d.×0.25 µL film thickness), which allowed for determination of cycloaddition products (para product and meta product) along with unreacted acrylic acid.

TiCl4-Catalyzed Cycloaddition of Acrylic Acid and Isoprene.

A 350 mL glass pressure vessel (10.3 bar max) equipped with a magnetic stir bar was charged with $TiCl_4$ (3.04 g, 16.0 mmol) at room temperature under Ar in a glove bag. The flask was sealed with a rubber septum in the glove bag and acrylic acid (57.7 g, 800 mmol) was added to the sealed pressure vessel via syringe. After mixing $TiCl_4$ with acrylic acid the Ar atmosphere was not required. The resulting red-brown solution was cooled in an ice bath followed by addition of isoprene (54.5 g, 800 mmol). The rubber septum was replaced by a pressure vessel screw cap (15 mm PTFE bushing with Viton® O-ring). After removing the ice bath 2 h following the addition of isoprene 2, the reaction mixture was allowed to warm to rt. Solid began to precipitate from solution after 8 h and the reaction was complete after 24 h at rt. A heterogeneous reaction crude containing substantial solid precipitate was transferred to a round bottom flask equipped with a side-arm and a magnetic stir bar. After addition of heptane (600 mL) and isopropanol (80 mL), the dissolved reaction crude was heated to 80° C. with stirring for 1 h. This homogeneous solution was extracted with 10% dilute aqueous $H_2SO_4$ (1×160 mL) followed by water (2×160 mL). An organic layer was dried over $MgSO_4$ and concentrated to afford 105 g (94%) of a white solid containing 4-methylcyclohex-3-enecarboxylic acid and 3-methylcyclohex-3-enecarboxylic acid as a 23:1 mixture. This solid was dissolved in a minimal amount of hot hexanes, crystallized at room temperature, filtered and dried to afford 90.3 g (81%) of purified para product as needle-like crystals. $^1H$ NMR (CDCl3) for 4-methylcyclohex-3-enecarboxylic acid: δ=1.63 (s, 3H), 1.70 (m, 1H), 1.92-2.26 (m, 3H), 2.16-2.28 (m, 2H), 2.50 (m, 1H), 5.40 (s, 1H). $^{13}C$ NMR (125 MHz, CDCl3) δ=23.5, 25.2, 27.4, 29.1, 39.0, 119.0, 138.8, 182.5.

Uncatalyzed Cycloaddition of Acrylic Acid 1 and Isoprene 2.

Acrylic acid (71.4 g, 0.991 mol) was added to isoprene (77.5 g, 1.14 mol) 2 under $N_2$ in a Parr Series 4575 high pressure reactor interfaced with a Series 4842 temperature controller. The reactor was flushed with $N_2$ and then pressurized to 8.3 bar with $N_2$. Heating the reactor at 95° C. with stirring (100 rpm) for 2 h led to an initial increase in pressure to 13.8 bar followed by a decline in pressure to 9.7 bar. After allowing the reactor to cool, a yellow heterogeneous reaction crude was obtained containing a 79% yield of a 3.2:1 ratio of para:meta (83.2 g of 4-methylcyclohex-3-ene-1-carboxylic acid and 26.9 g of 3-methylcyclohex-3-ene-1-carboxylic acid). $^1H$ NMR (CDCl$_3$) for 3-methylcyclohex-3-ene-1-carboxylic acid: 1.63 (s, 3H), 1.72 (m, 1H), 1.95-2.02 (m, 3H), 2.23-2.24 (m, 2H), 2.49 (m, 1H), 5.35-5.37 (m, 1H). Crude product was submitted to repeat crystallizations from hexanes to obtain 37.5 g (27% yield) pure 4-methylcyclohex-3-ene-1-carboxylic acid. $^1H$ NMR (CDCl$_3$): δ=1.63 (s, 3H), 1.69 (m, 1H), 1.96-2.04 (m, 3H), 2.20-2.27 (m, 2H), 2.52 (m, 1H), 5.36 (m, 1H).

Screening of Lewis Acid Cycloaddition Catalysts.

Various Lewis acids were screened to determine their ability to catalyze cycloaddition reactions under neat conditions. The Lewis acids tested were CuCl, $CuCl_2$, $NiCl_2$, $YCl_3$, $FeCl_2$, $AlCl_3$, $FeCl_3$, $ZnCl_2$, $MgCl_2$, $TiCl_3$, $SnCl_4$, $ScCl_3$, $SnCl_2$, $HfCl_4$, $ZrCl_4$, and $TiCl_4$. Screening of Lewis acids as catalysts for the cycloaddition of acrylic acid and isoprene employed a 15 mL glass pressure vessel (10.3 bar max) equipped with a magnetic stir bar that was charged with 0.5 mmol of Lewis acid under $N_2$ in a glove bag and sealed with a rubber septum. Solvent (4 mL) was then added to create a suspension if necessary. Acrylic acid (0.36 g, 5 mmol) was added via syringe. A color change was often observed (sometimes immediately, sometimes delayed) after addition of acrylic acid to the Lewis acid. When added, triethylamine, diisopropylethylamine, or 2,6-lutidine (0.5 mmol) were introduced following the addition of acrylic acid. Isoprene (0.41 g, 6 mmol) was finally added via syringe and the rubber septum replaced by a pressure vessel screw cap (15 mm PTFE bushing with Viton® O-ring). The reaction mixture was allowed to stir for 24 h, and the resulting crude analyzed by NMR and GC. In two additional reactions, TiCl4 was used as the Lewis acid catalyst and the reaction proceeded for either 48 hours at 0° C. or 100 hours at −20° C. A summary of the results is presented in Table 1.

TABLE 1

Cycloaddition[a] of Acrylic Acid and Isoprene

| Entry | Catalyst | Temp | Yield[b] | para/meta[c] |
|---|---|---|---|---|
| 1 | None | rt | 27% | 3:1 |
| 2 | CuCl | rt | 8% | 3:1 |
| 3 | $CuCl_2$ | rt | 8% | 3:1 |
| 4 | $NiCl_2$ | rt | 11% | 3:1 |
| 5 | $YCl_3$ | rt | 11% | 4:1 |
| 6 | $FeCl_2$ | rt | 11% | 4:1 |
| 7 | $AlCl_3$ | rt | 15% | 6:1 |
| 8 | $FeCl_3$ | rt | 17% | 7:1 |
| 9 | $ZnCl_2$ | rt | 20% | 5:1 |
| 10 | $MgCl_2$ | rt | 21% | 4:1 |
| 11 | $TiCl_3$ | rt | 34% | 8:1 |
| 12 | $SnCl_4$ | rt | 37% | 11:1 |
| 13 | $ScCl_3$ | rt | 48% | 8:1 |
| 14 | $SnCl_2$ | rt | 59% | 15:1 |
| 15 | $HfCl_4$ | rt | 73% | 12:1 |
| 16 | $ZrCl_4$ | rt | 76% | 12:1 |
| 17 | $TiCl_4$ | rt | 93% | 23:1 |
| 18[d] | $TiCl_4$ | 0° C. | 94% | 37:1 |
| 19[e] | $TiCl_4$ | −20° C. | 94% | 50:1 |

[a]Neat reaction for 24 h of 5 mmol/5 mmol, 1/2 using 2 mol % catalyst.
[b]Determined by NMR.
[c]Determined by GC.
[d]48 h reaction.
[e]100 h reaction.

Entry 1 of Table 1 is an uncatalyzed control reaction. As shown in the table, the uncatalyzed reaction of neat acrylic acid and neat isoprene (1/1, mol/mol) afforded a 27% yield with 3:1 para:meta selectivity. In entries 2-17, a Lewis acid catalyst was used with chloride as a counteranion. Significant improvements in yield and selectivity were observed for the $Sc^{3+}$, $Sn^{2+}$, $Hf^{4+}$, and $Zr^{4+}$ catalysts (entries 13-16). However, $Ti^{4+}$ was superior to the other catalysts under the same conditions (entry 17). As shown by entries 18 and 19, lowering the temperature improved the selectivity of $TiCl_4$-catalyzed cycloadditions of acrylic acid with isoprene.

Most terephthalic acid goes into the manufacture of poly(ethylene terephthalate) (PET), which is used in clear packaging and polyester fiber. PET also contains small amounts (3%) of isophthalic acid, which is used to interfere with PET crystallization thereby enhancing the transparency and lowering the melting point of PET. The cycloaddition reaction sequence (FIG. 1) could thus enable manufacture of 100% biobased PET by virtue of providing access to both biobased terephthalic acid and biobased isophthalic acid. Pure terephthalic acid derived from TiCl4-catalyzed cycloaddition could conceivably be combined with the mixture of terephthalic acid and isophthalic acid derived from the uncatalyzed cycloaddition to obtain the ratio of para:meta products required in PET manufacture.

EXAMPLE 3

$H_2SO_4$ Oxidation of 4-Methylcyclohex-3-Ene-1-Carboxylic Acid to p-Toluic Acid Concentrated sulfuric acid (4.21 mL, 79.0 mmol) was added dropwise to a solid (1.05 g, 7.49 mmol) composed of 97% (mol/mol) 4-methylcyclohex-3-ene-1-carboxylic acid and 3% 3-methylcyclohex-3-ene-1-carboxylic acid to form a mixture. The mixture was heated to 100° C. Vigorous gas formation was first observed when the reaction mixture temperature reached 60° C. Heating of the reaction mixture at 100° C. was continued until gas formation ceased. The reaction mixture was heated for a total of 12.25 minutes from the time when gas evolution was first observed at 60° C. The reaction mixture was poured into ice (20 g) immediately after gas formation ceased, and 0.89 g of a tan solid precipitated from solution.

A first crop of solid was collected with vacuum filtration and determined to be 98% pure p-toluic acid by HPLC (response factor based on a calibration curve using authentic p-toluic acid). The filtrate was extracted with EtOAc (3×), and combined organic layers were dried over $MgSO_4$ and concentrated to afford 0.072 g of a brown second crop determined to be 54% pure by HPLC. Based on the two crops of p-toluic acid obtained and the purity of each individual crop, a combined 91% yield of p-toluic acid was obtained. The first crop was dissolved in EtOAc and filtered through a plug of silica gel followed by further washing of the silica gel with EtOAc. The EtOAc filtrate was concentrated in vacuo and the residue recrystallized in p-xylene at rt to afford 0.75 mg of p-toluic acid in 73% yield. Recrystallized p-toluic acid was 99% pure based on HPLC analysis. $^1H$ NMR ($CDCl_3$): δ 7.99 (d, 2H), 7.26 (d, 2H), 2.42 (s, 3H).

EXAMPLE 4

Catalytic Dehydrogenation of a Mixture of 4-Methylcyclohex-3-Ene-1-Carboxylic Acid and 3-Methylcyclohex-3-Ene-1-Carboxylic Acid to a Mixture of p-Toluic Acid and m-Toluic Acid 5% Pd on C (0.35 g, 0.17 mmol) and 5.8 mL of p-xylene (bp 138° C.) were added to a 1.00 g (7.13 mmol) 56%/44% mixture of (3-methylcyclohex-3-ene-1-carboxylic acid/4-methylcyclohex-3-enecarboxylic acid) to form a suspension. The suspension was refluxed for 6.5 hours under air and then filtered through Celite®. Concentration of the filtrate afforded 0.93 g of a residue. Based on the composition of the residue as determined by HPLC, a 35% yield of m-toluic acid and a 34% yield p-toluic acid was obtained. Saturated cis- and trans-4-methylcyclohexyl-1-carboxylic acids were also formed based on $^1H$ NMR comparison with authentic samples. The ratio of p-toluic acid/trans-4-methylcyclohexyl-1-carboxylic acid/cis-4-methylcyclohexyl-1-carboxylic acid was 1.6/1.4/1, mol/mol/mol. $^1H$ NMR resonances associated with cis- and trans-3-methylcyclohexyl-1-carboxylic acids were also observed although authentic samples of these byproducts were not available.

EXAMPLE 5

Catalytic Dehydrogenation of a Mixture of 4-Methylcyclohex-3-Ene-1-Carboxylic Acid and 3-Methylcyclohex-3-Ene-1-Carboxylic Acid to a Mixture of p-Toluic Acid 5 and m-Toluic Acid Pd (II) trifluoroacetic acid (38.4 mg, 0.116 mmol), p-toluenesulfonic acid (83.6 mg, 0.439 mmol), mesitylene (0.61 mL), and 2-(dimethylamino)pyridine (24.7 mg, 0.202 mmol) were added to a 0.285 g (2.04 mmol) 56%/44% mixture of (3-methylcyclohex-3-ene-1-carboxylic acid/4-methylcyclohex-3-enecarboxylic acid) to form a mixture. The mixture was sparged with oxygen for 15 minutes and then heated to 100° C. for 48 hours under oxygen. The mixture was filtered and the filtrate was concentrated to a residue (0.259 g). Based on the composition of the residue as determined by $^1H$-NMR, an 18% yield of m-toluic acid and a 34% yield p-toluic acid was obtained. No resonances associated with trans-4-methylcyclohexyl-1-carboxylic acid, cis-4-methylcyclohexyl-1-carboxylic acid, trans-3-methylcyclohexyl-1-carboxylic acid, or cis-3-methylcyclohexyl-1-carboxylic acids were observed.

EXAMPLE 6

Dehydrogenation and Oxidation Reactions $H_2SO_4$ Oxidation of 4-Methylcyclohex-3-Ene-1-Carboxylic Acid to p-Toluic Acid.

Concentrated $H_2SO_4$ (80.0 mL, 1.50 mol) previously chilled in an ice bath was added dropwise to (20.1 g, 143 mmol) of 4-methylcyclohex-3-ene-1-carboxylic acid (para product from a $TiCl_4$-catalyzed cycloaddition) in a 250 mL round bottom flask chilled in an ice bath and fitted with a reflux condenser open to the atmosphere. The solution was heated to 100° C. Vigorous gas formation was first observed when the reaction mixture temperature reached 60° C. Heating of the reaction mixture at 100° C. was continued until gas formation ceased. The reaction mixture was heated for a total of 50 min from the time gas evolution was first observed at 60° C. The reaction mixture was poured into ice (400 g) immediately after gas formation ceased, and 17.7 g of a tan-colored solid precipitated from solution. This solid was collected by filtration to afford 15.4 g (79%) of p-toluic acid. Kugelrohr distillation (50 mL bulbs, 14/20 joint size) of this solid through a plug (9 cm×1.7 cm) of chromatographic grade silica gel (60 Å pore size, 40-63 μm mesh) under vacuum afforded 15.2 g (78%) of p-toluic acid as a white solid.

Dehydrogenation of 4-Methylcyclohex-3-Ene-1-Carboxylic Acid to p-Toluic Acid.

Davisil Grade 643 silica gel (150 Å pore size, 35-70 μm mesh) (1.77 g) was dried in a vacuum oven (150° C., 11 mm) overnight. 5% Pd on C (0.37 g, 0.085 mmol) containing approximately 50 wt % water was dried for 3 h under reduced pressure at 70° C. The dried silica gel and dried 5% Pd on C were thoroughly mixed and then packed into a 9 cm×1.7 cm glass tube using glass wool to immobilize the plug reactor material. 4-Methylcyclohex-3-ene-1-carboxylic acid (10.1 g, 72.0 mmol), para product from a TiCl4-catalyzed cycloaddition, was placed in a 50 mL, 14/20 round bottom flask. Vaporization/dehydrogenation of 4-methylcyclohex-3-ene-1-carboxylic employed a Kugelrohr apparatus assembled as follows: the 50 mL flask containing para product, the 9 cm×1.7 cm glass tube containing the plug reactor, three 50 mL collection bulbs in series, a U-shaped tube, and finally a straight gas adaptor connected to a water recirculating aspirator pump. The flask containing the para product and plug reactor was inserted into the Kugelrohr oven. The second 50 mL collection bulb and U-shaped tube were cooled to −78° C. Vaporization/dehydrogenation proceeded at 240° C. under vacuum (80 mm) with reciprocal oscillating agitation. A white solid accumulated in the collection bulbs and the U-shaped tube and was collected with EtOH washes. The plug reactor contents were suspended in EtOH followed by filtration to remove the Pd on C and silica gel. All of the EtOH washes were combined, concentrated and dried to afford 7.51 g (77%) of p-toluic acid, 1.24 g (12%) of trans-4-methylcyclohexane-1-carboxylic acid, and 0.93 g (9%) of cis-4-methylcyclohexane-1-carboxylic acid.

Homogeneous Oxidation of 4-Methylcyclohex-3-Ene-1-Carboxylic Acid to p-Toluic Acid.

In a glass test tube (15 cm×2 cm), Pd (II) trifluoroacetic acid (0.0327 g, 0.0984 mmol), p-toluenesulfonic acid (0.0760 g, 0.400 mmol), 2-(dimethylamino)pyridine (0.0245 g, 0.201 mmol), 0.276 g (1.97 mmol) of 4-methylcyclohex-3-enecarboxylic acid (para product from a TiCl$_4$-catalyzed cycloaddition) and mesitylene (0.90 mL) were added with a magnetic stir bar. The mixture was sparged with oxygen for 15 min and then heated to 100° C. for 24 h under O$_2$ (balloon). The reaction mixture was quenched with HOH (10 mL) and the resulting aqueous suspension was extracted with EtOAc. Drying and concentration afforded 0.0435 g (16%) of p-toluic acid.

H$_2$SO$_4$ Oxidation of a Mixture of 4-Methylcyclohex-3-Ene-1-Carboxylic Acid and 3-Methylcyclohex-3-Ene-1-Carboxylic Acid to p-Toluic Acid and m-Toluic Acid.

H$_2$SO$_4$ (3.99 mL, 74.9 mmol) previously chilled in an ice bath was added dropwise to an uncatalyzed cycloaddition product mixture consisting of 4-methylcyclohex-3-ene-1-carboxylic acid (0.446 g, 3.18 mmol) and 3-methylcyclohex-3-ene-1-carboxylic acid (0.562 g, 4.01 mmol) in a 15 mL round bottom flask chilled in an ice bath and fitted with a reflux condenser open to the atmosphere to generate a reaction mixture. The mixture was heated to 100° C. Vigorous gas formation was first observed when the reaction mixture temperature reached 60° C. Heating of the reaction mixture at 100° C. was continued until gas formation ceased. The reaction mixture was heated for a total of 13 min from the time gas evolution was first observed at 60° C. The reaction mixture was poured into ice (20 g) immediately after gas formation ceased, and 0.630 g of a tan-colored solid precipitated from solution. This solid was collected by filtration to afford 0.286 g (66%) of p-toluic acid and 0.0477 g (9%) of m-toluic acid.

Dehydrogenation of a Mixture of 4-Methylcyclohex-3-Ene-1-Carboxylic Acid and 3-Methylcyclohex-3-Ene-1-Carboxylic Acid to p-Toluic Acid and m-Toluic Acid.

Davisil Grade 643 silica gel (150 Å pore size, 35-70 µm mesh) (1.80 g) was dried in a vacuum oven (150° C., 11 mm) overnight. 5% Pd on C (0.37 g, 0.085 mmol) containing approximately 50 wt % water was dried for 3 h under reduced pressure at 70° C. The dried silica gel and dried 5% Pd on C were thoroughly mixed and then packed into a 9 cm×1.7 cm glass tube using glass wool to immobilize the plug reactor material. A mixture of 4-methylcyclohex-3-ene-1-carboxylic acid (8.00 g, 57.1 mmol) and 3-methylcyclohex-3-ene-1-carboxylic acid (2.61 g, 18.6 mmol), para and meta products, respectively, resulting from an uncatalyzed cycloaddition, was placed in a 50 mL, 14/20 round bottom flask. Vaporization/dehydrogenation of the mixture of 4-methylcyclohex-3-ene-1-carboxylic acid and 3-methylcyclohex-3-ene-1-carboxylic acid employed a Kugelrohr apparatus assembled as follows: the 50 mL flask containing 3, the 9 cm×1.7 cm glass tube containing the plug reactor, three 50 mL collection bulbs in series, a U-shaped tube, and finally a straight gas adaptor connected to a water recirculating aspirator pump. The flask containing para product and plug reactor were inserted into the Kugelrohr oven. The second 50 mL collection bulb and U-shaped tube were cooled to −78° C. Vaporization/dehydrogenation proceeded at 240° C. under vacuum (80 mm) with reciprocal oscillating agitation. A white solid accumulated in the collection bulbs and the U-shaped tube, which was collected with EtOH washes. The plug reactor contents were suspended in EtOH followed by filtration to remove the Pd on C and silica gel. All of the EtOH washes were combined, concentrated and dried to afford 4.08 g (53%) of p-toluic acid, 0.17 g (2%) of trans-4-methylcyclohexane-1-carboxylic acid, 0.05 g (1%) of cis-4-methylcyclohexane-1-carboxylic acid, 2.23 g (28%) of unreacted 4-methylcyclohex-3-ene-1-carboxylic acid, 1.74 g (69%) of m-toluic acid, 0.34 g (13%) of cis-3-methylcyclohexane-1-carboxylic acid, 0.27 g (10%) of trans-3-methylcyclohexane-1-carboxylic acid and 0.44 g (17%) of unreacted 3-methylcyclohex-3-ene-1-carboxylic acid.

EXAMPLE 7

Oxidation of p-Toluic Acid to Terephthalic Acid

Acetic acid (25 mL) was added to a mixture of manganese (II) acetate (8.7 mg, 50 µmol), cobalt(II) acetate tetrahydrate (14 mg, 56 µmol), N-hydroxysuccinimide (120 mg, 1.04 mmol), and p-toluic acid 5 (1.318 g, 9.681 mmol) to form a mixture. The mixture was stirred under O$_2$ at 100° C. for 24 hours. The mixture was then cooled, filtered, and dried under vacuum to afford an off-white solid (1.50 g). The off-white solid was determined by HPLC to contain terephthalic acid (1.46 g) as well as trace amounts of 4-formylbenzoic acid and unreacted p-toluic acid. The yield of terephthalic acid 6 was 91%. 1H NMR (DMSO): δ 13.270 (br, 2H), 8.037 (s, 4H).

EXAMPLE 8

Oxidation Reactions to Generate Terephthalic Acid and Isophthalic Acid

Oxidation of p-Toluic Acid to Terephthalic Acid.

To a one-neck 50-mL round bottom flask was added 1.088 g of p-toluic acid (containing 7.5 mol % of cyclohexanecarboxylic acid) followed by adding 9.96 mg of Co(OAc)$_2$.4H$_2$O (0.5 mol %), 6.9 mg of Mn(OAc)$_2$ (0.5 mol %) and 92 mg of N-hydroxysuccinimide (10 mol %). After adding 15 mL of HOAc, the flask was purged with O$_2$ for one min. Then a balloon with O$_2$ was connected to the flask. The reaction was stirred at 100° C. for 22 h. After cooling to room temperature, the solid was vacuum filtrated and washed with HOAc. Finally, 1186 mg of a white solid was obtained. Terephthalic acid and 4-formylbenzoic acid were obtained in 94% and 1% yields, respectively. Of the starting p-toluic acid, 2% remained unreacted. Terephthalic acid: ¹H NMR (DMSO) δ=8.04 (s, 4H), 13.3 (br s, 2H). ¹³C NMR (125 MHz, DMSO) δ=129.9, 134.9, 167.1

Oxidation of p-Xylene.

Using the above (for p-toluic acid) oxidation procedure for p-xylene oxidation, terephthalic acid, 4-formylbenzoic acid, and p-toluic acid were obtained in 69%, 3% and 5% yield, respectively.

Oxidation of m-Toluic Acid to Isophthalic Acid.

The reaction was performed at 1.088 g (8 mmol) scale of pure m-toluic acid. Using the above procedure (for p-toluic acid oxidation), 1164 mg of isophthalic acid was obtained as a white solid in 88% yield. ¹H NMR (DMSO) δ=7.62 (dd, J=7.8 Hz, 7.8 Hz, 1H), 8.12 (dd, J=2.0 Hz, 7.8 Hz, 2H), 8.46 (dd, J=1.5 Hz, 1.5 Hz, 1H), 13.3 (br s, 2H). ¹³C NMR (125 MHz, DMSO) δ=129.6, 130.4, 131.6, 133.8, 167.0.

EXAMPLE 9

Cycloaddition Reactions with Dienophile Carboxylic Acids

General Reaction Procedure, Product Purification and Characterization.

To a solution of acrylic acid (1.035 mL, 15 mmol) was added 35 μL of $TiCl_4$ (2 mol %) under $N_2$ at room temperature. Then, the solution was cooled down to 0° C. and stirred for 5 minutes before adding 2,3-dimethylbutylidene (3.4 mL, 30 mmol). After completion of the reaction, crude was extracted with 50 mL of 20% $H_2SO_4$ and 60 mL of hexanes, twice. After removing solvents under vacuum, the crude residue was purified by flash chromatography using gradient diethyl ether/hexanes; 1:6-1:5 as mobile phase to give 1.884 g (12.2 mmol) of a white solid in 82% yield. The results are summarized in Table 2.

4-methylcyclohex-3-enecarboxylic acid

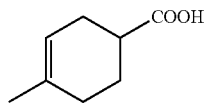

¹H NMR (500 MHz, CDCl3) δ=1.63 (s, 3H), 1.70 (m, 1H), 1.92-2.26 (m, 3H), 2.16-2.28 (m, 2H), 2.50 (m, 1H), 5.40 (s, 1H). ¹³C NMR (125 MHz, CDCl3) δ=23.5, 25.2, 27.4, 29.1, 39.0, 119.0, 138.8, 182.5.

3,4-dimethylcyclohex-3-enecarboxylic acid

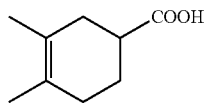

¹H NMR (500 MHz, CDCl3) δ=1.62 (s, 3H), 1.64 (s, 3H), 1.68 (m, 1H), 1.96-2.10 (m, 3H), 2.12-2.28 (m, 2H), 2.58 (m, 1H). ¹³C NMR (125 MHz, CDCl3) δ=18.8, 19.0, 25.6, 31.0, 33.7, 40.0, 123.7, 125.4, 182.8.

Cyclohex-3-enecarboxylic acid

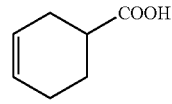

The reaction was performed at 4 mmol scale of acrylic acid and set up under −78° C. in a 15-mL pressured vessel. After the reaction was done at room temperature, the crude was loaded on silica column directly without aqueous workup. Chromatographic purification (EtOAc:hexanes=1:5) gave 431 mg of a colorless oil in 86% yield. ¹H NMR (500 MHz, CDCl3) δ=1.68-1.76 (m, 1H), 2.02-2.18 (m, 3H), 2.22-2.34 (m, 2H), 2.57-2.65 (m, 1H), 5.65-5.73 (m, 2H), 12.27 (bs, 1H). ¹³C NMR (125 MHz, CDCl3) δ=24.3, 24.8, 27.1, 39.2, 125.0, 126.7, 182.8.

Bicyclo[2.2.2]oct-5-ene-2-carboxylic acid

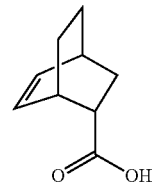 [SMILES: O=C(O)C1CC2C=CC1CC2]

The reaction was performed at 4 mmol scale of acrylic acid. After the reaction was done, the crude was loaded on silica column directly without aqueous workup. Chromatographic purification (EtOAc:hexanes=1:5 to 1:4) gave 507 mg of a white solid in 84% yield. ¹H NMR (500 MHz, CDCl3) δ=1.18-1.32 (m, 2H), 1.43-1.50 (m, 1H), 1.53-1.60 (m, 1H), 1.60-1.68 (m, 1H), 1.70-1.78 (m, 1H), 2.58 (m, 1H), 2.64 (m, 1H), 2.95 (m, 1H), 6.15 (dd, J=6.4 Hz, 6.4 Hz, 1H). 6.30 (dd, J=7.4 Hz, 7.4 Hz, 1H), 12.1 (br s, 1H). ¹³C NMR (125 MHz, CDCl3) δ=24.4, 25.4, 29.3, 29.6, 32.4, 42.7, 131.3, 135.2, 182.3.

Bicyclo[2.2.1]hept-5-ene-2-carboxylic Acid

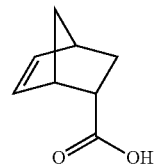

The reaction was performed at 4 mmol scale of acrylic acid. Chromatographic purification (Et2O:hexanes=1:5 to 2:3) gave 535 mg yellow oil, which was dissolved in 50 mL of 1M NaOH and washed with 50 mL dichloromethane twice. The aqueous was then acidified with HCl to pH=1, and extracted with 50 mL of dichloromethane twice, giving 448 mg of a colorless oil in 82% yield. Endo-product 1H NMR (500 MHz, CDCl3) δ=1.29 (d, J=7.8 Hz, 1H), 1.36-1.48 (m, 2H), 1.93 (m, 1H), 2.94 (s, 1H), 2.98 (dt, J=3.9 Hz, 9.3 Hz, 1H), 3.24 (s, 1H), 6.00 (dd, J=3.0 Hz, 5.4 Hz, 1H), 6.21 (dd, J=3.0 Hz, 5.8 Hz, 1H), 11.8 (br s, 1H). 13C NMR (125 MHz, CDCl3) δ=29.1, 42.5, 43.3, 45.7, 49.7, 132.5, 137.9, 181.6.

6-Acetyl-3-methylcyclohex-3-enecarboxylic Acid

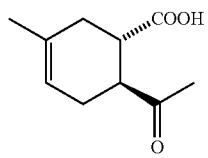

The reaction was performed at 2 mmol scale of 3-acetylacrylic acid. The procedure was the same as before except that isoprene and acrylic acid were mixed together before adding TiCl$_4$. After the reaction was done, the crude was loaded on silica column directly without aqueous workup. Chromatographic purification (EtOAc:hexanes=1:3 to 100:0) gave 300 mg of a white solid in 82% yield. Meta-product $^1$H NMR (500 MHz, CDCl$_3$) δ=1.65 (s, 3H), 1.90 (m, 1H), 2.09 (m, 1H), 2.20 (s, 3H), 2.26-2.44 (m, 2H), 2.82-2.88 (m, 2H), 5.40 (s, 1H), 11.8 (br s, 1H). $^{13}$C NMR (125 MHz, CDCl$_3$) δ=22.9, 27.7, 28.8, 32.6, 41.2, 47.5, 118.8, 132.6, 181.5, 211.3.

3-Methyl-6-(4-methylbenzoyl)cyclohex-3-enecarboxylic Acid

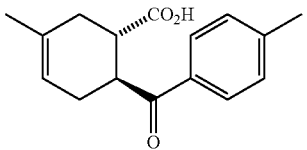

The reaction was performed at 2 mmol scale of 3-(4-methylbenzoyl)acrylic acid. The procedure was the same as before except that isoprene and acrylic acid were mixed together before adding TiCl4. After the reaction was done, the crude was loaded on silica column directly without aqueous workup. Chromatographic purification (EtOAc:hexanes=1:3 to 1:2) gave 446 mg of a white foam-like solid in 86% yield. Meta-product $^1$H NMR (500 MHz, CDCl3) δ=1.70 (s, 3H), 1.95 (m, 1H), 2.20 (m, 1H), 2.39 (s, 1H), 3.11 (dt, J=5.8 Hz, 11.3 Hz, 1H), 3.70 (dt, J=5.4 Hz, 11.4 Hz, 1H), 7.22 (d, J=7.8 Hz, 2H). 7.85 (d, J=7.3 Hz, 2H), 12.0 (br s, 1H). $^{13}$C NMR (125 MHz, CDCl3) δ=21.6, 23.1, 29.5, 32.9, 41.7, 43.3, 119.3, 128.7, 129.4, 132.6, 133.5, 140.0, 181.9, 202.5.

TABLE 2

Cycloaddition[a] of various dienes and dienophile carboxylic acids

| Entry | Substrates mol:mol | Time Temperature TiCl$_4$ mol % | Product | Yield[b] (Yield)[c] |
|---|---|---|---|---|
| 1 | (isoprene + acrylic acid) 2:1 | 22 h, rt, 2 mol % | (3,4-dimethylcyclohex-3-enecarboxylic acid) | 82% (13%) |
| 2 | (cyclohexadiene + acrylic acid) 2:1 | 0.7 h, 0° C., 2 mol % | (bicyclic norbornene carboxylic acid) exo/endo; 84:16 | 82% (31%) |
| 3 | (cyclopentadiene + acrylic acid) 2:1 | 23 h, rt, 10 mol % | (norbornene carboxylic acid) exo/endo; 99:1 | 84% (3%) |
| 4 | (butadiene + acrylic acid) 2:1 | 18 h, rt, 10 mol % | (cyclohex-3-enecarboxylic acid) | 86 (4%) |

TABLE 2-continued

Cycloaddition[a] of various dienes and dienophile carboxylic acids

| Entry | Substrates mol:mol | Time Temperature TiCl$_4$ mol % | Product | Yield[b] (Yield)[c] |
|---|---|---|---|---|
| 5 | 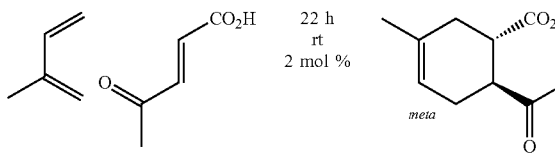<br>10:1 | 22 h<br>rt<br>2 mol % | 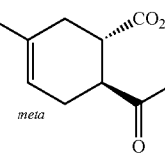<br>meta/para; 69:31 | 82%<br>(14%) |
| 6 | 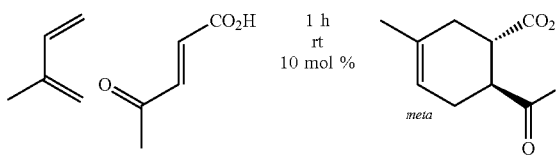<br>10:1<br>R = 4-Me—C$_6$H$_4$ | 1 h<br>rt<br>10 mol % | 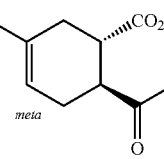<br>meta/para; 70:30 | 88%<br>(0) |

[a]Neat reaction.
[b]Isolated yield for TiCl$_4$-catalyzed cycloaddition.
[c]NMR yield of control cycloaddition lacking TiCl$_4$.

As shown in Table 2, reaction of acrylic acid with 2,3-dimethylbutene, 1,3-cyclohexadiene, cyclpentadiene, and 1,3-butadiene all gave yields using TiCl$_4$ well in excess of the control reactions lacking catalysts (entries 1-4). Similar improvements over control yields were realized in the TiCl$_4$-catalyzed reactions of isoprene with β-acylacrylic acids (entries 4 and 5). Cycloadditions of dienophile carboxylic acids catalyzed by TiCl$_4$ require neat reaction conditions. A quantity of liquid diene is required to dissolve (entries 1-4) or at least partially solubilize the dienophile carboxylic acids (entries 5 and 6).

Non-Limiting Discussion of Terminology

The headings (such as "Introduction" and "Summary") and sub-headings used herein are intended only for general organization of topics within the present technology, and are not intended to limit the disclosure of the present technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting ingredients, components or process steps, Applicants specifically envision embodiments consisting of, or consisting essentially of, such ingredients, components or processes excluding additional ingredients, components or processes (for consisting of) and excluding additional ingredients, components or processes affecting the novel properties of the embodiment (for consisting essentially of), even though such additional ingredients, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein

What is claimed is:

1. A method for producing terephthalic acid, isophthalic acid or both terephthalic acid and isophthalic acid, comprising:
    (a) reacting isoprene with acrylic acid in the presence of a first catalyst to form a first product selected from the group consisting of 4-methyl-3-cyclohexene-1-carboxylic acid, 3-methyl-3-cyclohexene-1-carboxylic acid, and mixtures thereof;
    (b) performing an aromatization reaction on the first product to form a second product selected from the group consisting of para-toluic acid, meta-toluic acid, and mixtures thereof; and
    (c) performing an oxidation reaction on the second product in the presence of a third catalyst to form terephthalic acid, isophthalic acid, or mixtures thereof.

2. The method according to claim 1, wherein the first catalyst is a Lewis acid catalyst, wherein the Lewis acid catalyst comprises an aluminum, copper, hafnium, magnesium, nickel, iron, yttrium, zinc, zirconium, scandium, tin, or titanium cation, and comprises a triflates, chlorides, or bromides counterion.

3. The method according to claim 2, wherein the Lewis acid catalyst is selected from the group consisting of CuCl, $CuCl_2$, $NiCl_2$, $YCl_3$, $FeCl_2$, $AlCl_3$, $FeCl_3$, $ZnCl_2$, $MgCl_2$, $TiCl_3$, $SnCl_4$, $ScCl_3$, $SnCl_2$, $HfCl_4$, $ZrCl_4$, and $TiCl_4$.

4. The method according to claim 1, wherein the reaction of the isoprene with the acrylic acid is performed under neat conditions.

5. The method according to claim 1, wherein the reaction is maintained at room temperature for from about 1 hour to about 48 hours.

6. The method according to claim 1, wherein the reaction is maintained at from about −20° C. to about 30° C. for from about 48 hours to about 100 hours.

7. The method according to claim 1, wherein the first catalyst is boronic acid or 2-bromophenyl boronic acid.

8. The method according to claim 1, wherein the aromatization reaction is conducted in the presence of sulfuric acid or acetic anhydride solvent.

9. The method according to claim 1, wherein the aromatization reaction is conducted in the presence of a catalyst selected from the group consisting of chromium, molybdenum, iridium, rhodium, ruthenium, nickel, palladium, platinum, vanadium, iron and manganese.

10. The method according to claim 1, wherein the aromatization reaction is a vapor phase dehydrogenation conducted using a second catalyst, optionally selected from the group consisting of chromium, molybdenum, iridium, rhodium, ruthenium, nickel, palladium, and platinum.

11. The method according to claim 10, wherein the second catalyst is a Pd on C catalyst and the bio-4-methyl-3-cyclohexene-1-carboxylic acid, bio-3-methyl-3-cyclohexene-1-carboxylic acid, or mixture thereof is distilled at from about 50 mm to about 100 mm and from about 100° C. to about 300° C. through the Pd on C catalyst dispersed in macroporous silica gel.

12. The method according to claim 1, wherein the third catalyst is a $Co(OAc)_2/Mn(OAc)_2$ catalyst in acetic acid solvent.

13. The method according to claim 1, wherein the third catalyst is an N-hydroxyimide catalyst, preferably selected from the group consisting of N-hydroxyphthalimide (NHPI), N-hydroxysuccinimide (NHSI), N-hydroxy-1,8-naphthalimide (NHNI), and carbonic acid tert-butyl phthalimido ester (CATPE).

14. The method according to claim 1, wherein one or both of the isoprene and the acrylic acid are bio-based.

15. A method for producing a substituted bio-terephthalates and/or substituted bio-isophthalates comprising:
    (a) reacting bio-isoprene, with a substituted bio-alkene to form a first bio-product;
    (b) aromatizing the first bio-product to form a second bio-product; and
    (c) oxidizing the second bio-product to form the substituted bio-terephthalate and/or substituted bio-isophthalate.

16. The method according to claim 15, wherein the substituted bio-alkene is bio-cinnamic acid, bio-fumaric acid, or bio-maleic acid.

17. A method for producing terephthalic acid and/or isophthalic acid, and derivatives thereof, comprising:
    (a) performing a neat cycloaddition reaction by reacting bio-isoprene with a bio-dienophile in the presence of a $TiCl_4$ catalyst to form a first bio-product;
    (b) performing an aromatization on the first product to form a second bio-product by distilling the first product with a Pd(0) on C catalyst to generate the second product; and
    (c) performing an oxidation reaction on the second bio-product, by reacting the second bio-product with a $Co(OAc)_2/Mn(OAc)_2$ catalyst in acetic acid with a N-hydroxysuccinimide radical chain carrier, form bio-terephthalic acid, bio-isophthalic acid, or combinations thereof.

18. The method according to claim 17, wherein the cycloaddition reaction and is conducted at about ambient temperature.

19. The method according to claim 17, wherein the bio-dienophile is bio-acrylic acid.

20. A method of making poly(ethylene terephthalate) comprising:
    (a) reacting isoprene with acrylic acid in the presence of a first catalyst to produce 4-methyl-3-cyclohexene-1-carboxylic acid and 3-methyl-3-cyclohexene-1-carboxylic acid;
    (b) performing an aromatization reaction on the 4-methyl-3-cyclohexene-1-carboxylic acid and the 3-methyl-3-cyclohexene-1-carboxylic acid to produce para-toluic acid and meta-toluic acid;

(c) performing an oxidation reaction on the para-toluic acid and the meta-toluic acid in the presence of a third catalyst to form terephthalic acid and isophthalic acid; and (d) polymerizing the terephthalic acid and the isophthalic acid with ethylene glycol to produce poly(ethylene terephthalate).

21. The method of claim 20, wherein one or both of the isoprene and acrylic acid are bio-based.

* * * * *

UNITED STATES PATENT AND TRADEMARK OFFICE
CERTIFICATE OF CORRECTION

PATENT NO. : 9,499,465 B2
APPLICATION NO. : 14/775149
DATED : November 22, 2016
INVENTOR(S) : John Frost It is certified that error appears in the above-identified patent and that said Letters Patent is hereby corrected as shown below:

In the Drawings

Drawing Sheet 4 of 4, Figure 4, "TiCl4" should be --$TiCl_4$--.

In the Specification

Column 8, Line 22, "TiCl4" should be --$TiCl_4$--.

Column 11, Line 14, "TiCl4-Catalyzed" should be --$TiCl_4$-Catalyzed--.

Column 11, Line 45, "(CDCl3)" should be --($CDCl_3$)--.

Column 11, Line 48, "CDCl3)" should be --$CDCl_3$)--.

Column 12, Line 27, "TiCl4" should be --$TiCl_4$--.

Column 13, Line 10, "TiCl4-Catalyzed" should be --$TiCl_4$-Catalyzed--.

Column 15, Lines 3 - 4, "TiCl4-Catalyzed" should be --$TiCl_4$-Catalyzed--.

Column 17, Line 49, "CDCl3)" should be --$CDCl_3$)--.

Column 17, Line 51, "CDCl3)" should be --$CDCl_3$)--.

Column 17, Line 64, "CDCl3)" should be --$CDCl_3$)--.

Column 17, Line 66, "CDCl3)" should be --$CDCl_3$)--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,499,465 B2

Column 18, Line 16, "CDCl3)" should be --CDCl$_3$)--.
Column 18, Line 18, "CDCl3)" should be --CDCl$_3$)--.

Column 18, Line 39, "CDCl3)" should be --CDCl$_3$)--.

Column 18, Line 43, "CDCl3)" should be --CDCl$_3$)--.

Column 18, Line 65, "CDCl3)" should be --CDCl$_3$)--.

Column 19, Line 2, "CDCl3)" should be --CDCl$_3$)--.

Column 20, Line 17, "TiCl4." should be --TiCl$_4$.--.

Column 20, Line 21, "CDCl3)" should be --CDCl$_3$)--.

Column 20, Line 25, "CDCl3)" should be --CDCl$_3$)--.

Column 21, Table 2, Entry 6, Lines 1-27

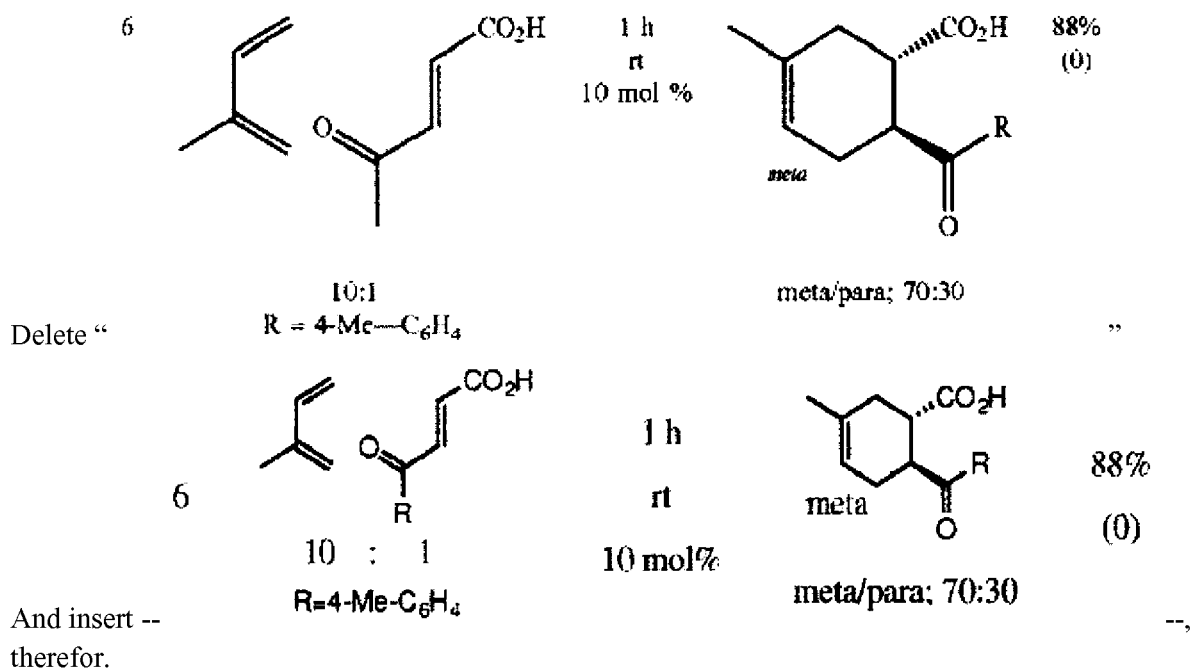

Delete " ... "

And insert -- ... -- therefor.

Column 23, Line 21, "herein" should be --.--.